US010125108B2

(12) United States Patent
Jahn et al.

(10) Patent No.: US 10,125,108 B2
(45) Date of Patent: Nov. 13, 2018

(54) PROCESS FOR THE EPOXIDATION OF PROPENE

(71) Applicants: Robert Jahn, Rodenbach (DE); Wolfgang Wöll, Maintal (DE); Bernd Jaeger, Bickenbach (DE); Matthias Pascaly, Frankfurt (DE)

(72) Inventors: Robert Jahn, Rodenbach (DE); Wolfgang Wöll, Maintal (DE); Bernd Jaeger, Bickenbach (DE); Matthias Pascaly, Frankfurt (DE)

(73) Assignees: EVONIK DEGUSSA GMBH, Essen (DE); THYSSENKRUPP INDUSTRIAL SOLUTIONS, Essen (DE)

( * ) Notice: Subject to any disclaimer, the term of this patent is extended or adjusted under 35 U.S.C. 154(b) by 0 days.

(21) Appl. No.: 15/570,167

(22) PCT Filed: Apr. 19, 2016

(86) PCT No.: PCT/EP2016/058638
§ 371 (c)(1),
(2) Date: Oct. 27, 2017

(87) PCT Pub. No.: WO2016/173887
PCT Pub. Date: Nov. 3, 2016

(65) Prior Publication Data
US 2018/0134676 A1 May 17, 2018

(30) Foreign Application Priority Data

Apr. 28, 2015 (EP) .................................. 15165410

(51) Int. Cl.
*C07D 301/12* (2006.01)
*C07D 303/04* (2006.01)
*B01D 3/34* (2006.01)
*B01D 3/42* (2006.01)
*B01D 19/04* (2006.01)
*B01J 29/89* (2006.01)
*C07D 301/36* (2006.01)

(52) U.S. Cl.
CPC ............. *C07D 301/12* (2013.01); *B01D 3/34* (2013.01); *B01D 3/4294* (2013.01); *B01D 19/0409* (2013.01); *B01J 29/89* (2013.01); *C07D 301/36* (2013.01); *C07D 303/04* (2013.01)

(58) Field of Classification Search
CPC .. C07D 301/12; C07D 301/36; C07D 303/04; B01D 3/34; B01D 3/4294; B01D 19/0409
USPC .......................................................... 549/531
See application file for complete search history.

(56) References Cited

U.S. PATENT DOCUMENTS

| 4,410,501 | A | 10/1983 | Taramasso |
|---|---|---|---|
| 5,675,026 | A | 10/1997 | Thiele |
| 6,372,924 | B2 | 4/2002 | Thiele |
| 6,491,861 | B1 | 12/2002 | Grosch et al. |
| 6,710,002 | B2 | 3/2004 | Grosch |
| 6,756,503 | B2 | 6/2004 | Teles et al. |
| 6,849,162 | B2 | 2/2005 | Teles et al. |
| 7,157,610 | B2 | 1/2007 | Hofen et al. |
| 7,527,712 | B2 | 5/2009 | Bassler et al. |
| 8,735,612 | B2 | 5/2014 | Crampton |
| 2004/0110970 | A1* | 6/2004 | Haas ............... C07D 301/12 549/531 |
| 2009/0137851 | A1 | 5/2009 | Pottast et al. |
| 2013/0023683 | A1 | 1/2013 | Ruwwe et al. |
| 2014/0228589 | A1 | 8/2014 | Stepp et al. |
| 2017/0210718 | A1 | 7/2017 | Stochniol et al. |

FOREIGN PATENT DOCUMENTS

| EP | 0 100 119 | 2/1984 |
|---|---|---|
| EP | 0 230 949 | 8/1987 |
| EP | 0 712 852 | 5/1996 |
| EP | 0 814 058 | 12/1997 |
| EP | 1 247 805 | 10/2002 |

(Continued)

OTHER PUBLICATIONS

Alex C. M. Kuo, polydimethylsiloxane, Polymer Data Handbook, 1999, p. 411-435. (Year: 1999).*
International Search Report for PCT/EP2016/058638 filed Apr. 19, 2016.
Written Opinion of the International Searching Authority for PCT/EP2016/058638 filed Apr. 19, 2016.

(Continued)

*Primary Examiner* — Taylor V Oh
(74) *Attorney, Agent, or Firm* — Law Office of: Michael A. Sanzo, LLC

(57) ABSTRACT

In a process for the epoxidation of propene, comprising the steps: reacting propene with hydrogen peroxide in the presence of a titanium silicalite catalyst and a methanol solvent; separating non-reacted propene and propene oxide from the resulting reaction mixture to provide a solvent mixture comprising methanol and water in a combined amount of at least 90% by weight; and feeding this solvent mixture as a feed stream to a continuously operated methanol distillation column at a feed point in the middle section of said column to provide an overhead product comprising at least 90% by weight methanol and a bottoms product comprising at least 90% by weight water; the addition of a liquid defoamer, having a solubility in the feed stream of less than 10 mg/kg at 25° C. and a surface tension at the liquid air interface of less than 22 mN/m at 20° C., at or above the feed point in an amount exceeding the solubility of the liquid defoamer in the feed stream suppresses foam formation in the methanol distillation column.

20 Claims, No Drawings

(56) References Cited

FOREIGN PATENT DOCUMENTS

| RU | 2159675 | 11/2000 |
|----|---------|---------|
| WO | WO 97/47614 | 12/1997 |
| WO | WO 00/76989 | 12/2000 |
| WO | WO 01/57010 | 8/2001 |
| WO | WO 02/085873 | 10/2002 |
| WO | WO 03/093255 | 11/2003 |
| WO | WO 2004/048335 | 6/2004 |
| WO | WO 2005/000827 | 1/2005 |
| WO | WO 2006/001876 | 1/2006 |
| WO | WO 2008/151742 | 12/2008 |
| WO | WO 2007/074101 | 3/2010 |
| WO | WO 2011/064191 | 6/2011 |
| WO | WO 2011/119215 | 9/2011 |

OTHER PUBLICATIONS

International Preliminary Report on Patentability for PCT/ EP2016/058638 filed Apr. 19, 2016.
PCT Direct letter for PCT/ EP2016/058638 during international stage and dated Jan. 28, 2016.
U.S. Appl. No. 15/329,629, filed Jan. 27, 2017, US-2017/0210718 A1, Jul. 27, 2017, Stochniol.
Office Action for copending U.S. Appl. No. 15/329,626 dated Dec. 18, 2018.
Response to Office Action for copending U.S. Appl. No. 15/329,626, filed Mar. 18, 2018.
U.S. Appl. No. 15/778,318, filed May 23, 2018, Brendel, et al.
U.S. Appl. No. 15/778,337, filed May 23, 2018, Pascaly, et al.
U.S. Appl. No. 15/778,425, filed May 23, 2018, Hofen, et al.
U.S. Appl. No. 15/778,562, filed May 23, 2018, Wiederhold, et al.

* cited by examiner

PROCESS FOR THE EPOXIDATION OF PROPENE

CROSS REFERENCE TO RELATED APPLICATIONS

The present application is US national stage of international application PCT/EP2016/058638, which had an international filing date of Apr. 19, 2016, and which was published in English under PCT Article 21(2) on Nov. 3, 2016. Priority is claimed to European application EP 15165410.0, filed on Apr. 28, 2015.

The present invention relates to a process for the epoxidation of propene with hydrogen peroxide in the presence of a titanium silicalite catalyst and a methanol solvent where methanol is recovered.

The epoxidation of propene with hydrogen peroxide in the presence of a titanium silicalite catalyst is known from EP 0 100 119 A1. The epoxidation is usually carried out in the presence of a methanol solvent to achieve high reaction rates. Work up of the reaction mixture by separating non-reacted propene and propene oxide and subsequent distillation of a mixture comprising methanol and water as the major components for recovery of methanol has been described in the prior art, for example in WO 01/57010, WO 02/02544, WO 02/02545, WO 2004/009566 and WO 2006/066673.

It has now been found that the operation of a continuous distillation column separating methanol from a mixture comprising methanol and water, which mixture has been obtained by separating non-reacted propene and propene oxide from the reaction mixture resulting from the epoxidation of propene with hydrogen peroxide in the presence of a silicalite catalyst and a methanol solvent, can be troubled by foam formation inside the column, which severely impairs separation efficiency and column capacity. This problem of foam formation has not been recognized in the prior art. It has further been found that such foam formation can be effectively prevented by adding a liquid defoamer, having a surface tension at the liquid air interface lower than methanol and forming a separate liquid phase in the column, at or above the feed point to the column.

Subject of the invention is therefore a process for the epoxidation of propene, comprising the steps a) reacting propene with hydrogen peroxide in the presence of a titanium silicalite catalyst and a methanol solvent;

b) separating non-reacted propene and propene oxide from the reaction mixture obtained in step a) to provide a solvent mixture comprising methanol and water with a combined amount of methanol and water of at least 90% by weight; and c) feeding the solvent mixture obtained in step b) as a feed stream to a continuously operated methanol distillation column at a feed point in the middle section of said column providing an overhead product comprising at least 90% by weight methanol and a bottoms product comprising at least 90% by weight water;

wherein a liquid defoamer having a solubility in the feed stream of less than 10 mg/kg at 25° C. and a surface tension at the liquid air interface of less than 22 mN/m at 20° C. is added to the distillation column at or above the feed point in an amount exceeding the solubility of the liquid defoamer in the feed stream.

In step a) of the process of the invention, propene is reacted with hydrogen peroxide in the presence of a titanium silicalite catalyst and a methanol solvent to provide a reaction mixture containing propene oxide. Propene can be used as a technical mixture with propane, preferably containing from 0.1 to 15 vol-% of propane. Hydrogen peroxide can be used as an aqueous solution, preferably containing from 30 to 75% by weight hydrogen peroxide and most preferably from 40 to 70% by weight. The titanium silicalite catalyst preferably has an MFI or MEL crystal structure, and most preferably titanium silicalite-1 with MFI structure as known from EP 0 100 119 A1, is used. The titanium silicalite catalyst is preferably employed as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation, silica being preferred as binder. Extrudates with a diameter of 1 to 5 mm are preferably used as fixed bed catalysts. The methanol solvent can be a technical grade methanol, a solvent stream recovered in the work-up of the epoxidation reaction mixture or a mixture of both.

The epoxidation reaction of step a) is preferably carried out at a temperature of 30 to 80° C., more preferably at 40 to 60° C., and a pressure of from 0.5 to 5 MPa, more preferably 1.5 to 3.5 MPa. The epoxidation reaction is preferably carried out with addition of ammonia to improve propene oxide selectivity as described in EP 0 230 949 A2. Ammonia is preferably added in an amount of from 100 to 3000 ppm based on the weight of hydrogen peroxide. The epoxidation is preferably carried out in a fixed bed reactor by passing a mixture comprising propene, hydrogen peroxide and methanol over the catalyst fixed bed. The fixed bed reactor is preferably equipped with cooling means and cooled with a liquid cooling medium. The temperature profile within this reactor is preferably maintained such that the cooling medium temperature of the cooling means is at least 40° C. and the maximum temperature within the catalyst bed is 60° C. at the most, preferably 55° C. The epoxidation reaction mixture is preferably passed through the catalyst bed in down flow mode, preferably with a superficial velocity from 1 to 100 m/h, more preferably 5 to 50 m/h, most preferred 5 to 30 m/h. The superficial velocity is defined as the ratio of volume flow rate/cross section of the catalyst bed. Additionally it is preferred to pass the reaction mixture through the catalyst bed with a liquid hourly space velocity (LHSV) from 1 to 20 $h^{-1}$, preferably 1.3 to 15 $h^{-1}$. It is particularly preferred to maintain the catalyst bed in a trickle bed state during the epoxidation reaction. Suitable conditions for maintaining the trickle bed state during the epoxidation reaction are disclosed in WO 02/085873 on page 8 line 23 to page 9 line 15. Propene is preferably employed in excess relative to the hydrogen peroxide in order to achieve high hydrogen peroxide conversion, the molar ratio of propene to hydrogen peroxide preferably being chosen in the range from 1.1 to 30. The methanol solvent is preferably used in the epoxidation in a weight ratio of 0.5 to 20 relative to the amount of aqueous hydrogen peroxide solution. The amount of catalyst employed may be varied within wide limits and is preferably chosen so that a hydrogen peroxide consumption of more than 90%, preferably more than 95%, is achieved within 1 minute to 5 hours under the employed epoxidation reaction conditions. Most preferably, the epoxidation reaction is carried out with a catalyst fixed bed maintained in a trickle bed state at a pressure close to the vapor pressure of propene at the reaction temperature, using an excess of propene that provides a reaction mixture comprising two liquid phases, a methanol rich phase and a propene rich liquid phase. Two or more fixed bed reactors may be operated in parallel or in series in order to be able to operate the epoxidation process continuously when regenerating the epoxidation catalyst. Regeneration of the epoxidation catalyst can be carried out by calcination, by treatment with a heated gas, preferably an oxygen containing gas or by a solvent wash, preferably by the periodic regeneration described in WO 2005/000827.

In step b) of the process of the invention, non-reacted propene and propene oxide formed in step a) are separated from the reaction mixture obtained in step a) to provide a solvent mixture comprising methanol and water with a combined amount of methanol and water of at least 90% by weight. Non-reacted propene can be separated by distillation or by depressurization, preferably in a flash evaporator. Propene oxide formed in step a) can be separated by distillation. Preferably, non-reacted propene is separated by depressurization to a pressure of from 0.16 to 0.30 MPa, followed by a propene oxide distillation stage where an overhead product containing propene oxide and from 20 to 60% of the methanol contained in the reaction mixture resulting in step a) is separated from a bottoms product containing water and the remainder of the methanol. This bottoms product can be fed as solvent mixture to step c) of the process of the invention.

In a preferred embodiment, the overhead product from the propene oxide distillation stage, optionally after removing residual propene by distillation, is subjected to an extractive distillation using water as extraction solvent. The bottoms product of the extractive distillation, comprising methanol and water, is thereafter combined with the bottoms product of the propene oxide distillation stage to give a solvent mixture containing methanol and water in a combined amount of at least 90% by weight. This solvent mixture may be fed directly to step c) of the process of the invention. The extractive distillation is preferably carried out with additional feeding of a compound containing an unsubstituted $NH_2$ group and capable of reacting with acetaldehyde during the extractive distillation, as described in WO 2004/048335.

In a preferred embodiment, the solvent mixture comprising methanol and water, obtained by removing non-reacted propene and propene oxide product, is subjected to a catalytic hydrogenation with hydrogen to remove non-reacted hydrogen peroxide remaining from step a), as described in WO 03/093255.

In step c) of the process of the invention, the solvent mixture separated in step b), comprising methanol and water with a combined amount of at least 90% by weight, is fed as a feed steam to a feed point in the middle section of a methanol distillation column. The methanol distillation column is operated continuously to provide an overhead product comprising at least 90% by weight methanol and a bottoms product comprising at least 90% by weight water. The methanol distillation column can be a plate column, a packed column or a column with a structured packing and preferably has from 10 to 40 theoretical separation stages. The methanol distillation column is preferably operated at a pressure of from 0.1 to 1.2 MPa.

A liquid defoamer having a solubility in the feed stream of less than 10 mg/kg at 25° C. and a surface tension at the liquid air interface of less than 22 mN/m at 20° C. is added to the methanol distillation column at or above the feed point. The liquid defoamer is added in an amount exceeding the solubility of the liquid defoamer in the feed stream. The liquid defoamer is preferably added in an amount of no more than 50 wppm and not less than 2 wppm calculated on the feed stream. A low solubility in the feed stream and an addition of defoamer in an amount exceeding the solubility is essential for achieving sufficient foam suppression in the methanol distillation column. Without wishing to be bound by theory, the inventors believe that both factors are necessary for maintaining a second liquid phase rich in defoamer in the column section below the feed point and that the presence of such a second liquid phase is necessary for efficient foam suppression inside the distillation column. A low surface tension of less than 22 mN/m is also essential for achieving sufficient foam suppression in the methanol distillation column. Defoamers having a higher surface tension provide insufficient foam suppression in the methanol distillation column, even if they are effective for foam suppression with aqueous solutions such as a column bottoms product containing less than 3% by weight methanol. Adding the liquid defoamer at or above the feed point is also important for achieving sufficient foam suppression in the methanol distillation column and adding the defoamer at the column reboiler will not suppress foam formation inside the column.

The liquid defoamer preferably comprises a polydimethylsiloxane and more preferably comprises more than 5% by weight polydimethylsiloxane. The polydimethylsiloxane preferably has a viscosity at 20° C. of from 500 to 1000 mPa*s determined with a falling ball viscosimeter according to DIN 53015. The liquid defoamer may additionally comprise hydrophobized silica particles, preferably hydrophobized amorphous silica particles and more preferably hydrophobized fumed silica particles. Most preferred are liquid defoamers comprising more than 5% by weight polydimethylsiloxane in combination with 0.5 to 4% by weight hydrophobized fumed silica particles. The liquid defoamer is preferably added in the form of an aqueous emulsion, preferably containing from 5 to 25% by weight liquid defoamer dispersed in an aqueous phase. Suitable aqueous emulsions comprising a polydimethylsiloxane and hydrophobized fumed silica particles are commercially available, for example TEGO® Antifoam WM 20 from Evonik Industries and DOW CORNING® DB-110A (EU) antifoam emulsion from Dow Corning.

The overhead product obtained in step c), comprising at least 90% by weight methanol, is preferably recycled to step a) and used as methanol solvent in the epoxidation reaction of step a).

In a preferred embodiment of the process, an acid is added in step c) at or above the feed point in an amount sufficient to protonate all ammonia and amines contained in the feed stream. The acid may be a mineral acid or a carboxylic acid. Suitable mineral acids are nitric acid, sulfuric acid, hydrochloric acid, phosphoric acid and perchloric acid. Preferred mineral acids are sulfuric acid and phosphoric acid. Carboxylic acids are preferably selected from C1 to C12 mono- or dicarboxylic acids such as formic acid, acetic acid, propionic acid, butyric acid, pentanoic acid, hexanoic acid, heptanoic acid, octanoic acid, nonanoic acid, decanoic acid, undecanoic acid or dodecanoic acid, oxalic acid, malonic acid, succinic acid, glutaric acid, adipic acid, maleic acid or fumaric acid. The most preferred carboxylic acid is acetic acid. The most preferred acid is sulfuric acid. The acid may be introduced into the methanol distillation column separately from the feed stream, combined with the feed stream or combined with the liquid defoamer. Preferably, the acid is added admixed with the liquid defoamer. Addition of an acid avoids recycling of amines with the methanol solvent and thereby reduces deactivation of the titanium silicalite catalyst by organic amines. Adding the acid admixed with the liquid defoamer simplifies layout and operation of the methanol distillation column.

EXAMPLES

Example 1

In a continuously operated pilot plant, a mixture comprising propene and hydrogen peroxide in a methanol solvent was passed through a fixed bed containing a titanium silicalite catalyst. Non-reacted propene and propene oxide were separated from the resulting reaction mixture by pressure reduction and distillation and a solvent mixture comprising 79% by weight of methanol, 18.6% by weight of water, 1% by weight of 1,2-propanediol, 0.5% by weight of 1-methoxy-2-propanol, 0.5% by weight of 2-methoxy-1-propanol and 0.3% by weight of other byproducts was recovered. 4.5 kg/h of this solvent mixture was fed as a feed stream to the middle section of a rectification column having 30 stages. 10-50 ml/h of a 10% by weight aqueous sulfuric acid solution was added to the feed stream immediately before feeding it to the column. The rectification column was operated continuously at a pressure of 0.6 MPa and a bottom temperature of 155 to 160° C., providing an overhead product containing more than 90% by weight methanol and a bottoms product containing more than 90% by weight water. During operation of the column foam formation was observed in the stripping section of the column.

Example 2

Example 1 was repeated with 20 mg/kg of the defoamer TEGO® Antifoam WM 20 being added to the feed stream. The defoamer TEGO® Antifoam WM20 has a surface tension at the liquid air interface of 20 mN/m at 20° C. and is insoluble in water and methanol. No foam formation was observed during operation of the column.

Example 3

Example 1 was repeated with 20 mg/kg of the defoamer TEGO® Antifoam 2290 being added to the feed stream. The defoamer TEGO® Antifoam 2290 has a surface tension at the liquid air interface of 30 mN/m at 20° C. and is insoluble in water and methanol. Foam formation was observed during operation of the column.

Example 4

Example 1 was repeated with 20 mg/kg of the defoamer TEGILOXAN 1000 being added to the feed stream. The defoamer TEGILOXAN 1000 has a solubility in the feed stream of more than 10 mg/kg at 25° C. and a surface tension at the liquid air interface of 20 mN/m at 20° C. Foam formation was observed during operation of the column.

The invention claimed is:

1. A process for the epoxidation of propene, comprising the steps:
   a) reacting propene with hydrogen peroxide in the presence of a titanium silicalite catalyst and a methanol solvent;
   b) separating non-reacted propene and propene oxide from the reaction mixture obtained in step a) to provide a solvent mixture comprising methanol and water with a combined amount of methanol and water of at least 90% by weight; and
   c) feeding the solvent mixture obtained in step b) as a feed stream to a continuously operated methanol distillation column at a feed point in the middle section of said column providing an overhead product comprising at least 90% by weight methanol and a bottoms product comprising at least 90% by weight water;
   wherein a liquid defoamer having a solubility in the feed stream of less than 10 mg/kg at 25° C. and a surface tension at the liquid air interface of less than 22 mN/m at 20° C. is added to the distillation column at or above the feed point in an amount exceeding the solubility of the liquid defoamer in the feed stream.

2. The process of claim 1, wherein the liquid defoamer comprises a polydimethylsiloxane.

3. The process of claim 2, wherein the liquid defoamer comprises more than 5% by weight polydimethylsiloxane.

4. The process of claim 1, wherein the liquid defoamer comprises hydrophobized silica particles.

5. The process of claim 1, wherein the liquid defoamer is added in an amount of from 2 to 50 wppm calculated on the feed stream.

6. The process of claim 1, wherein the overhead product obtained in step c) is recycled to step a).

7. The process of claim 1, wherein the liquid defoamer is added to the feed stream before feeding said feed stream to the methanol distillation column.

8. The process of claim 1, wherein ammonia is added in step a).

9. The process of claim 1, wherein an acid is added in step c) at or above the feed point in an amount sufficient to protonate all ammonia and amines contained in the feed stream.

10. The process of claim 9, wherein the acid is added admixed with the liquid defoamer.

11. The process of claim 3, wherein the liquid defoamer comprises hydrophobized silica particles.

12. The process of claim 3, wherein the liquid defoamer is added in an amount of from 2 to 50 wppm calculated on the feed stream.

13. The process of claim 3, wherein the overhead product obtained in step c) is recycled to step a).

14. The process of claim 3, wherein the liquid defoamer is added to the feed stream before feeding said feed stream to the methanol distillation column.

15. The process of claim 3, wherein ammonia is added in step a).

16. The process of claim 3, wherein an acid is added in step c) at or above the feed point in an amount sufficient to protonate all ammonia and amines contained in the feed stream.

17. The process of claim 13, wherein the liquid defoamer is added to the feed stream before feeding said feed stream to the methanol distillation column.

18. The process of claim 13, wherein the liquid defoamer is added to the feed stream before feeding said feed stream to the methanol distillation column.

19. The process of claim 13, wherein ammonia is added in step a).

20. The process of claim 13, wherein an acid is added in step c) at or above the feed point in an amount sufficient to protonate all ammonia and amines contained in the feed stream.

* * * * *